United States Patent
Rosenberg et al.

[11] Patent Number: 5,910,147
[45] Date of Patent: Jun. 8, 1999

[54] ANGLED REPLACEABLE COMEDONE EXTRACTOR

[75] Inventors: Mark R. Rosenberg, Paradise Valley, Ariz.; Donald J. Ersler, 725 Garvens Ave., Brookfield, Wis. 53005

[73] Assignee: Donald J. Ersler, Brookfield, Wis.

[21] Appl. No.: 09/017,356

[22] Filed: Feb. 2, 1998

Related U.S. Application Data

[63] Continuation-in-part of application No. 08/770,944, Dec. 31, 1996, abandoned.

[51] Int. Cl.$^6$ ..................................................... A61B 17/32
[52] U.S. Cl. ............................................ 606/131; 606/181
[58] Field of Search .................................. 606/131, 181, 606/182, 167; 132/286

[56] References Cited

U.S. PATENT DOCUMENTS

| | | | |
|---|---|---|---|
| 834,683 | 10/1906 | Severin . | |
| 896,338 | 8/1908 | Tolman | 606/131 |
| 906,085 | 12/1908 | Tolman | 606/131 |
| 1,842,403 | 1/1932 | Hunsaker et al. | 606/131 |
| 3,046,987 | 7/1962 | Ehrlich . | |
| 4,462,405 | 7/1984 | Erlich . | |
| 5,395,380 | 3/1995 | Berkovich | 606/131 |
| 5,454,828 | 10/1995 | Schraga | 606/181 |
| 5,571,128 | 11/1996 | Shapiro | 606/167 |

OTHER PUBLICATIONS

Mueller, The Surgical Armamentarium p. 10, 1980.
Photocopy of a Page From a Dermatology Cat. Showing Prior Art Tools, Company; Delasco, 608 13$^{th}$ Ave, Counsel Bluff, IA 51501.

*Primary Examiner*—Michael H. Thaler
*Attorney, Agent, or Firm*—Donald J. Ersler

[57] ABSTRACT

A replaceable comedone extractor includes a body, a pimple drain member and a lancet. The body has a length, and a substantial middle region shaped for being held by a thumb and forefinger. A first end of the body is formed into the shape of a pimple drain member. In a first preferred embodiment, the replaceable comedone extractor is intended to be replaceable, the lancet is molded into the second end of the body. In a second preferred embodiment, the replaceable comedone extractor has a second end which has a horizontal slot and at least one retaining notch formed therein to receive a disposable lancet. In a third preferred embodiment, the replaceable comedone extractor has a second end which has a horizontal bore formed therein to firmly receive a retractable lancet assembly. In a fourth preferred embodiment, an angled replaceable comedone extractor has a second end which is bent up toward the first end at an obtuse angle.

22 Claims, 3 Drawing Sheets

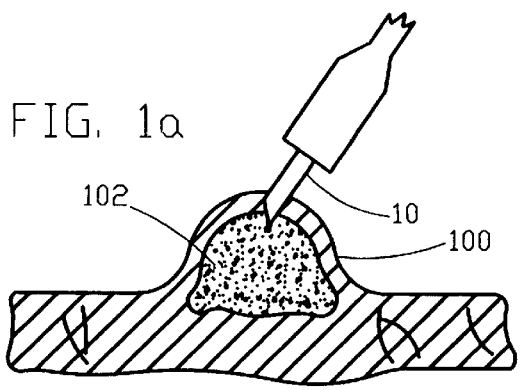
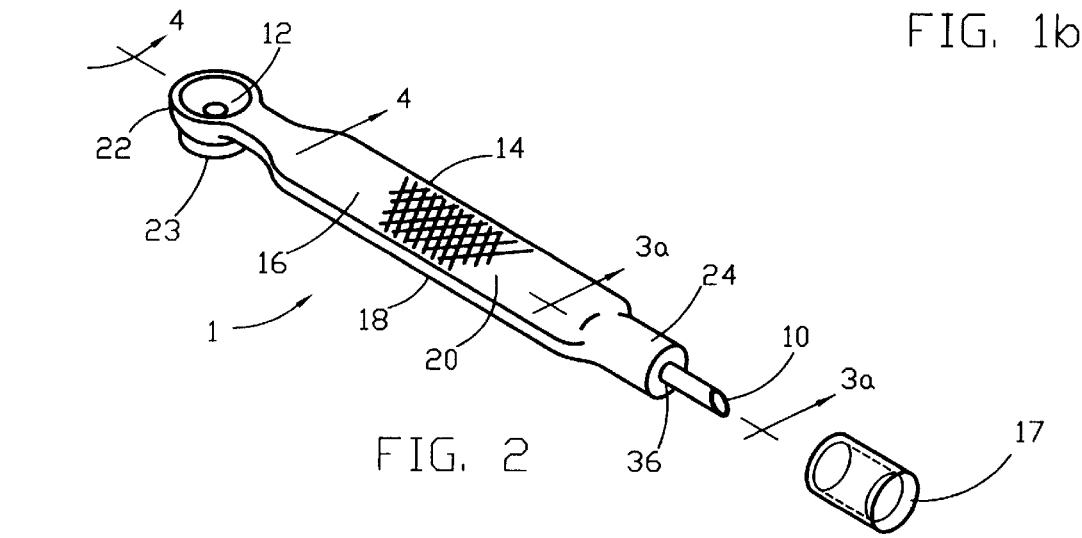
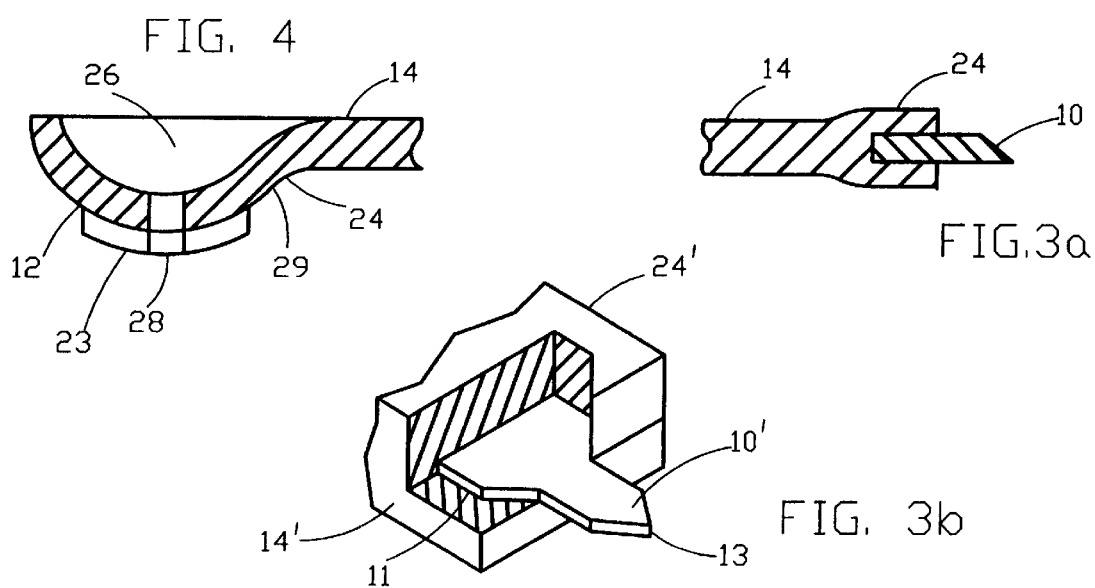

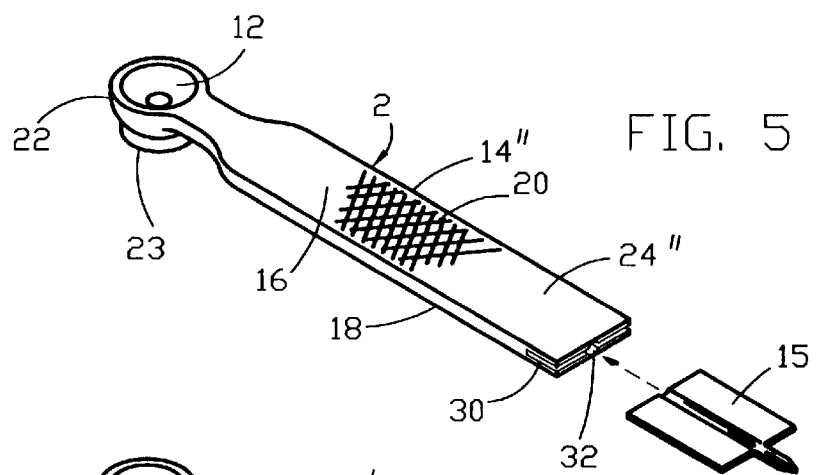
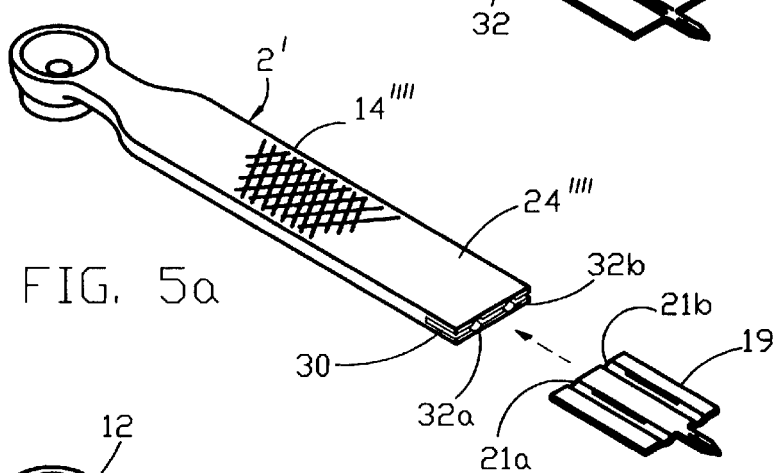
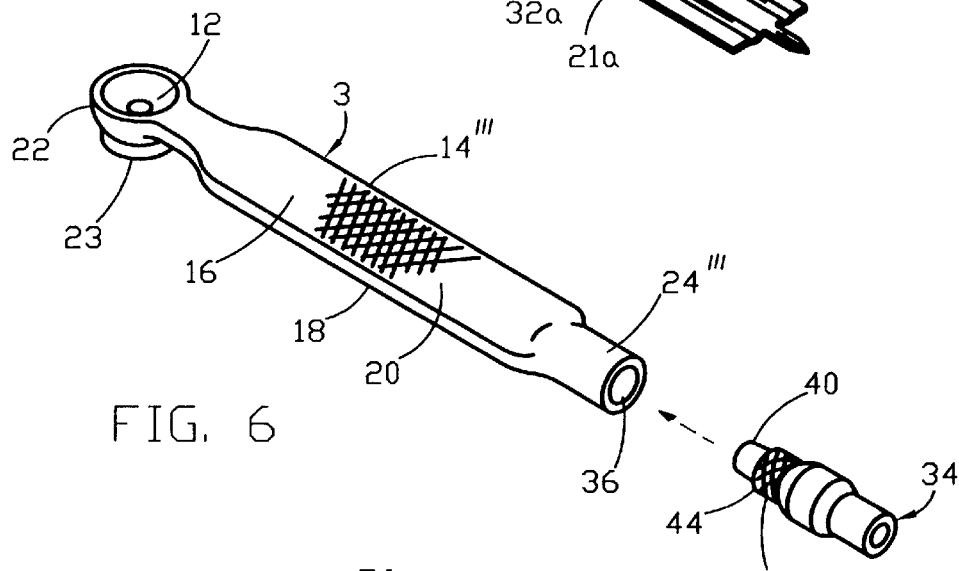
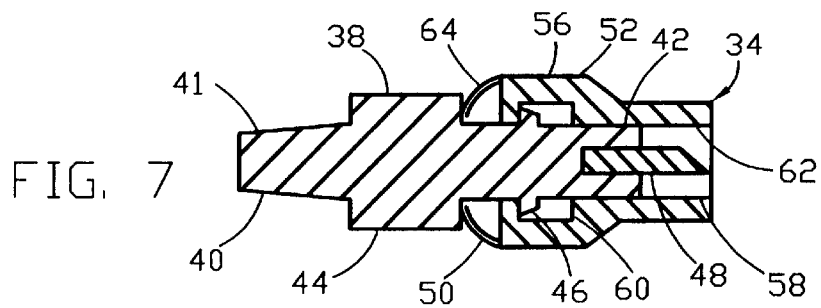

ANGLED REPLACEABLE COMEDONE EXTRACTOR

CROSS-REFERENCES TO RELATED APPLICATIONS

This is a continuation-in-part application, Ser. No. 08/770,944 filed on Dec. 31, 1996 now abandoned.

BACKGROUND OF THE INVENTION

1. Field of the Invention

The present invention relates generally to comedone extractors and more specifically to an angled replaceable comedone extractor which is shaped differently to provide better control to the user and is less expensive to manufacture than that of the prior art.

2. Discussion of the Prior Art

A comedone extractor is used to drain facial acne lesions, commonly referred to as pimples. Some designs have a pointed edge on one end to lance the pimple, and a pimple drain member on the other end to press out the matter inside the pimple. One prior art design has a pimple drain member on one end and a sharp tip on the other end. The drawback to this design is that the sharp tip will become dull after only a few applications and must be sent to a medical tool sharpening company for best results. The prior art design must also be sterilized before each and every use.

A second prior art design uses the pimple drain member on one end and a replaceable blade on the other. The drawback to this design is that the replaceable blade is very expensive. Each blade costs approximately $2.00, and must be appropriately discarded after each use according to OSHA regulations. There are other drawbacks to both of these prior art designs. Both prior art designs are fabricated from expensive stainless steel to endure endless sterilizations. Neither design has any means to protect the sharp tip from damage. Neither prior art design is tremendously safe to use; anyone who handles thereof, or is operated on by thereof can be accidentally pricked with the pointed tip of the lancet.

Further, the prior art designs have a straight body. The straight body is not the optimal design for manipulating the pimple draining member. The prior art designs also lack a cushioning device on the bottom of the comedone extractor portion. A pimple drain member which has a hard surface can induce scaring of a pimple that is being drained.

Accordingly, there is a clearly felt need in the art for an angled replaceable comedone extractor which is optimally shaped to allow better control, has a cushioned comedone extractor portion, can hold an economical replaceable lancet, can have a retractable replaceable lancet to prevent injury, and is economical enough to be disposable.

SUMMARY OF THE INVENTION

The primary objective of the present invention is to provide an angled replaceable comedone extractor which is optimally shaped to allow better control, has a cushioned comedone extractor portion, can hold an economical replaceable lancet, can have a retractable replaceable lancet to prevent injury, and is economical enough to be disposable.

According to the present invention, a replaceable comedone extractor includes a body, a pimple drain member, and a lancet. In a first preferred embodiment, the replaceable comedone extractor is intended to be disposable. The body of the replaceable comedone extractor has a first end, a second end, a length, and a substantial middle region of the length is shaped for being held by a thumb and forefinger. The first end is molded in the shape of a pimple drain member and the second end is molded around a short lancet. The pimple drain member has the shape of a round bottomed bore. A cushion pad is fastened to the bottom surface of the pimple drain member. A vertical hole passes through the bottom surface of the pimple drain member and the cushion pad. The cushion pad prevents trauma or injury to the pimple when too much pressure is applied by the pimple drain member. The lancet may be fabricated from a sharpened rod, a small metal stamping with a pointed tip, or from any suitable pointed material. The unit is sterilized after manufacture and is intended to be disposed of after usage.

In a second preferred embodiment, the replaceable comedone extractor has a disposable lancet. The body of the replaceable comedone extractor has a first end, a second end, a length, and a substantial middle region of the length is shaped for being held by a thumb and forefinger. The first end is formed in the shape of a pimple drain member, and the second end is a horizontal cavity which is specifically sized to firmly receive a disposable lancet. The pimple drain member has the shape of a round bottomed bore. A cushion pad is fastened to the bottom surface of the pimple drain member. A vertical hole passes through the bottom surface of the pimple drain member and the cushion pad. The disposable lancet is inserted into the horizontal cavity of the second end and is commonly of the type used for obtaining blood samples from a finger.

In a third preferred embodiment, the replaceable comedone extractor has a retractable lancet assembly. The body of the replaceable comedone extractor has a first end, a second end, a length, and a substantial middle region of the length is shaped for being held by a thumb and forefinger. The first end of the body is formed in the shape of a pimple drain member and the second end has a horizontal bore which is sized to firmly receive the retractable lancet assembly. The pimple drain member has the shape of a round bottomed bore. A cushion pad is fastened to the bottom surface of the pimple drain member. A vertical hole passes through the bottom surface of the pimple drain member and the cushion pad.

The retractable lancet assembly comprises a lancet, a shaft, a leaf spring, and a retractable cover. The shaft has a first end, a second end, and a shoulder. The second end of the body of the replaceable comedone extractor has a horizontal bore which is sized to firmly receive the first end of the shaft. A tapered shank is disposed at the first end of the shaft. A lancet is molded into the second end of the shaft such that a small part of the lancet protrudes from the second end. The outside diameter of the first end has a rough texture. The shoulder is disposed substantially in the middle of the shaft.

The retractable cover has a first end, a second end, a first bore, a second bore, and a length. The first bore originates at the first end and terminates at substantially the middle of the retractable cover. The second bore originates at the second end and is terminated by the bottom of the first bore. A diameter of the second bore is sized to slidably receive the second end of the shaft. A diameter of the first bore is sized to loosely receive the shoulder of the shaft. A lip is disposed at the first end of the retractable cover and is sized to capture the shoulder of the shaft, and allow limited lateral movement within the first bore. The inside diameter of the lip and the outside diameter of the shoulder are sized to allow the shoulder to be snapped into the first bore.

The leaf spring is molded as an integral part of the shaft at substantially the first end of the shaft, but thereof may also be designed to snap over the shoulder of the shaft. The assembly of the retractable lancet assembly is accomplished by snapping the retractable cover over the shoulder of the shaft. The leaf spring will force the retractable cover forward to protect a user or a patient from being accidently pricked. The retractable cover also protects the lancet from damage. The retractable cover will only travel backwards enough to allow the lancet to pierce the pimple. The retractable cover is preferably fabricated from a transparent plastic material to allow the user to see the pimple being lanced. The retractable lancet assembly is replaceable, the first end of retractable lancet assembly is inserted into the horizontal bore in the second end of the body.

In a fourth preferred embodiment, an angled replaceable comedone extractor is intended to be disposable and has a body which is angled to optimize use. The angled body of the replaceable comedone extractor has a first end, a second end, and a substantially angled middle region. The first end is molded in the shape of a pimple drain member and the second end is molded around a short lancet. The second end may also be shaped to accept a disposable lancet, or retractable lancet assembly. The pimple drain member has the shape of a round bottomed bore. A cushion pad is fastened to the bottom of the pimple drain member. A vertical hole passes through the bottom surface of the pimple drain member and the cushion pad. The cushion pad prevents trauma or injury to the pimple when to much pressure is applied by the pimple drain member. The unit is sterilized after manufacture and is intended to be disposed of after use.

Accordingly, it is an object of the present invention to provide an replaceable comedone extractor which can be economically manufactured.

It is a further object of the present invention to provide a replaceable comedone extractor which accepts an economical replaceable lancet.

It is yet a further object of the present invention to provide a replaceable comedone extractor which has a cushion pad which prevents trauma or injury to a pimple when it is pressed.

It is yet a further object of the present invention to provide an angled replaceable comedone extractor which has an angled body which provides better control and allows a user to more easily extract matter from a pimple.

Finally, it is another object of the present invention to provide a replaceable comedone extractor which has a replaceable retractable lancet which prevents injuries and protects the lancet.

These and additional objects, advantages, features and benefits of the present invention will become apparent from the following specification.

BRIEF DESCRIPTION OF THE DRAWINGS

FIG. 1a is a cross sectional view of a lancet piercing a pimple;

FIG. 1b is a cross sectional view of a pimple drain member extracting the contents of a pimple;

FIG. 2 is a perspective exploded detail view of a first preferred embodiment of a replaceable comedone extractor which is intended to be disposable in accordance with the present invention;

FIG. 3a is a cross sectional detail view of a lancet molded into a second end of a replaceable comedone extractor in accordance with the present invention;

FIG. 3b is a cut away detail view of a lancet molded into a second end of a replaceable comedone extractor in accordance with the present invention;

FIG. 4 is a cross sectional detail view of a pimple draining member at the first end of a replaceable comedone extractor in accordance with the present invention;

FIG. 5 is an exploded perspective view of a second preferred embodiment of a replaceable comedone extractor with a second end adapted to receive and retain disposable lancets in accordance with the present invention;

FIG. 5a is a perspective exploded view of the second end of the second preferred embodiment modified to receive a special disposable lancet in accordance with the present invention;

FIG. 6 is an exploded perspective view of a third preferred embodiment of a replaceable comedone extractor with a second end adapted to receive and retain a retractable lancet assembly in accordance with the present invention;

FIG. 7 is a cross sectional detail view of a retractable lancet assembly in accordance with the present invention;

DETAILED DESCRIPTION OF THE PREFERRED EMBODIMENTS

Figure 8:
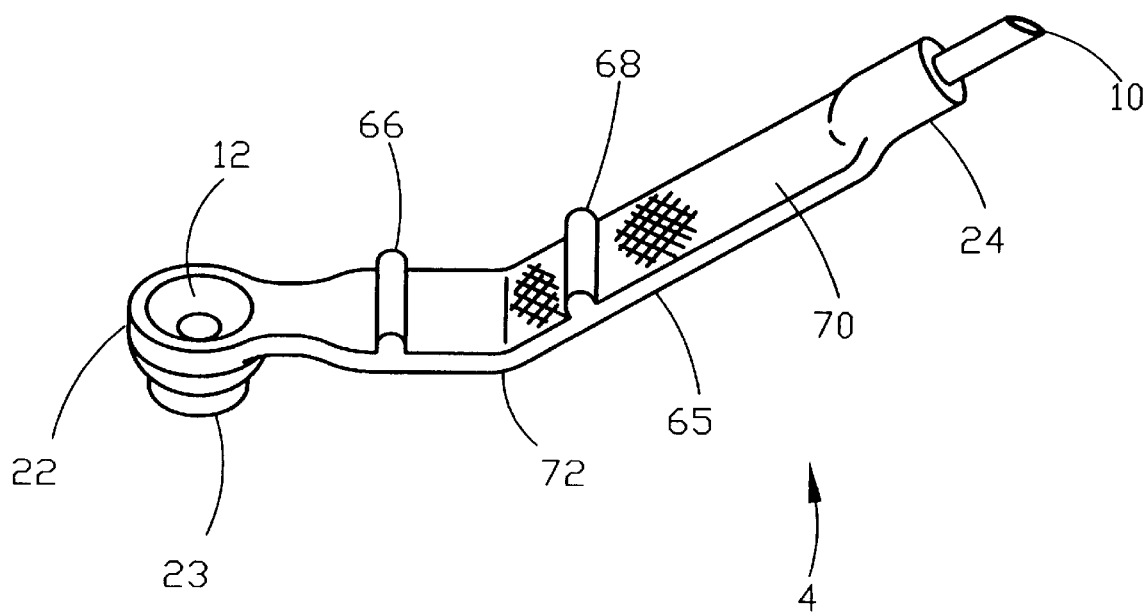
FIG. 8 is a perspective view of a fourth preferred embodiment of angled replaceable comedone extractor which is intended to be disposable in accordance with the present invention.

With reference now to the drawings, and particularly to FIGS. 1a and 1b, there is shown a cross sectional view of a lancet 10 piercing a pimple 100, and a cross sectional view of a pimple drain member 12 extracting the contents of a pimple 102, respectively. The best way to remove a pimple 100 without scaring a patient's face is to create an opening in the pimple 100 with a lancet 10, then apply pressure with a pimple drain member 12 to remove the matter 102 inside the pimple 100.

FIG. 2 shows a perspective exploded detail view of a replaceable comedone extractor 1 which is intended to be disposable. The replaceable comedone extractor 1 includes a lancet 10, a pimple drain member 12, and a body 14. The body 14 has a length, a top surface 16, a bottom surface 18, a first end 22, and a second end 24. A substantial middle region of the body 14 is shaped for being held by a thumb and a forefinger. The body is fabricated from an inexpensive yet strong plastic material. The top surface 16 and the bottom surface 18 at substantially the middle of the body has a rough surface 20 to improve grip for the thumb and forefinger.

The first end 22 of the body 14 is molded into the shape of a pimple drain member 12 and the second end 24 is molded around a lancet 10. With reference to FIG. 4, the pimple drain member 12 has the shape of a round bottomed bore 26. A cushion pad 23 is fastened to the bottom surface 29 of the pimple drain member 12. The cushion pad 23 is fabricated from a material which is compressible yet has memory to return to its original thickness; such a material could be an easily compressible rubber, a close cell foam, or any suitable material. A vertical hole 28 passes through the bottom surface 29 of the pimple drain member 12 and the cushion pad 23.

With reference to FIG. 3a, the lancet 10 is fabricated from a sharpened rod, and molded into the second end 24 of the body 14. With reference to FIG. 3b, the lancet 10' is fabricated from a small metal stamping with a body 11 and a pointed tip 13. The second end 24 of the body 14 may also be molded into a sharp point. The replaceable comedone extractor 1 is sterilized after manufacture and intended for one time use. A cap 17 may also be placed over the second end 24 to protect the lancet 10 from damage.

FIG. 5 shows a second preferred embodiment of a replaceable comedone extractor 2 with a disposable lancet 15. The replaceable comedone extractor 2 includes a pimple drain member 12, and a body 14". The body 14" has a length, a top surface 16, a bottom surface 18, a first end 22, and a second end 24". A substantially middle region of the body 14" is shaped for being held by a thumb and a forefinger. The body 14 is fabricated from an inexpensive yet strong plastic material or stainless steel. The top surface 16 and the bottom surface 18 at substantially the middle region of the body has a rough surface 20 to improve grip for the thumb and forefinger.

The first end 22 of the body 14" is formed into the shape of a pimple drain member 12. With reference to FIG. 4, the pimple drain member 22 has the shape of a round bottomed bore 26. The cushion pad 23 is fastened to the bottom surface 29 of the pimple drain member 12. A vertical hole 28 passes through the bottom surface 29 of the pimple drain member 12 and cushion pad 23. The second end 24" of the body 14" has a horizontal slot 30 and at least one retaining notch 32; only one notch is required, two are shown. The disposable lancet 15 is an off-the-shelf item, commonly used for obtaining blood samples. The horizontal slot 32 is sized to firmly receive the disposable lancet 15. The retaining notch 32 prevents lateral movement of the disposable lancet 15. Most disposable lancets have a longitudinal channel which transverses the entire length thereof. The replaceable comedone extractor 2 must be sterilized before each use. The disposable lancet 15 is easily and cheaply replaceable. When the disposable lancet 15 becomes dull, it is removed and replaced with another lancet for $0.02 to $0.04 as opposed to the $2.00 required for replacement of the prior art blade design.

FIG. 5a shows a perspective exploded view of the second end 24"" of the second preferred embodiment 2' modified to receive a special disposable lancet 19. The special disposable lancet 19 has two longitudinal channels 21a and 21b which transverse the length thereof instead of the one longitudinal channel of disposable lancet 15. The second end 24"" has been modified to have two retaining notches 32a and 32b which receive the two longitudinal channels 21a and 21b of the special disposable lancet 19. The second longitudinal channel of special disposable lancet 19 helps prevent lateral movement thereof while retained in the second end 24"" of the body 14"".

FIG. 6 shows a third preferred embodiment of a replaceable comedone extractor 3 with a second end 24"' adapted to retain a retractable lancet assembly 34. The replaceable comedone extractor 3 includes a pimple drain member 12, a body 14"', and a retractable lancet assembly 34. The body 14"' has a length, a top surface 16, a bottom surface 18, a first end 22, and a second end 24"'. A substantial middle region of the body 14"' is shaped for being held by a thumb and a forefinger. The body 14"' may be fabricated from plastic or stainless steel. The top surface 16 and the bottom surface 18 at substantially the middle region of the body 14"' has a rough surface 20 to improve grip for a thumb and forefinger.

The first end 22 of the body 14"' is formed into the shape of a pimple drain member 12. With reference to FIG. 4, the pimple drain member 22 has the shape of a round bottomed bore 26. The cushion pad 23 is fastened to the bottom surface 29 of the pimple drain member 12. A vertical hole 28 passes through the bottom surface 29 of the pimple drain member 12 and cushion pad 23. With reference to FIG. 7, the second end 24 of the body 14"' has a horizontal bore 36 which is sized to firmly receive a tapered shank 41 disposed at a first end 40 of the retractable lancet assembly 34. The tapered shank 41 has a taper of between one to four degrees. A retractable lancet assembly 34 includes a lancet 48, a leaf spring 50, a retractable cover 52, and the shaft 38. The shaft 38 has the a first end 40, a second end 42, an outside diameter 44, and a shoulder 46. A lancet 48 is molded into the second end 42 of the shaft 38 such that a small portion the lancet 48 protrudes from the second end 42 of the shaft 38. The outside diameter 44 is disposed at substantially the first end 40 of the shaft 38. The outside diameter 44 has a rough texture 54 to aid removal and insertion of the retractable lancet assembly 34 from the replaceable comedone extractor 3. The shoulder 46 is disposed substantially at the middle of the shaft 38.

The retractable cover 52 has a length, a first end 56, a second end 58, a first bore 60, and a second bore 62. The first bore 60 originates at the first end 56 of the retractable cover 34 and terminates at substantially the middle of the length. The second bore 62 originates at the second end 58 of the retractable cover 52 and is terminated by a bottom of the first bore 60. A diameter of the second bore 62 of the retractable cover 52 is sized to slidably receive the second end 42 of the shaft 38. The diameter of the first bore 60 is sized to loosely receive the shoulder 46 of the shaft 38. A lip 64 disposed at the first end of the retractable cover 52 is sized to capture the shoulder 46 of the shaft 38 and allow limited lateral movement within the first bore 60. The inside diameter of the lip 64 is sized to allow the shoulder 46 of the shaft 38 to be snapped into the first bore 60. The outside of the lip 64 and the inside of the shoulder 46 have a radius or chamfered surface to facilitate easy assembly. The lip 64 may be formed by ultrasonically welding a separate piece on the first end 56 or by swaging material from the first end 56 to form thereof.

The leaf spring 50 is molded as part of the shaft 38 at the end of the first shoulder 44, but may also be designed to snap over the shoulder 46 of the shaft 38. The assembly of the retractable lancet assembly 34 is accomplished by snapping the retractable cover 34 over the second shoulder 46 of the shaft 38. The leaf spring 50 forces the retractable cover 52 forward to protect a user or patient from being accidently pricked. The retractable cover 52 also protects the lancet 48 from damage. The retractable cover 52 will only travel backwards enough to allow the lancet 48 to pierce a pimple. The retractable cover 52 is preferably fabricated from a transparent plastic material to allow the user to see a pimple being lanced. The retractable lancet assembly 34 may be replaced when the lancet 48 becomes too dull.

FIG. 8 shows a perspective view of an angled replaceable comedone extractor 4 which is intended to be disposable. The angled replaceable comedone extractor 4 includes a lancet 10, a pimple drain member 12, and an angled body 65. The angled body 65 has a second end 24 which is bent upward at angle relative to the first end 22 instead of being straight as the body 14. It is preferable that the value of the obtuse angle be 135 degrees. The angled body 65 provides better control and makes it easier to drain a pimple than the straight prior art designs. A first rib 66 and a second rib 68 may be formed on a top surface 70 to position a thumb during use. Either or both of the top surface 70 and a bottom surface 72 may be roughened to improve grip between a thumb and forefinger. The angled body 65 is fabricated from an inexpensive yet strong plastic material.

The first end 22 of the angled body 65 is molded into the shape of a pimple drain member 12 and the second end 24 is molded around a lancet 10. It is also possible to mold the lancet 10 as part of the second end 24. The second end 24 may also be shaped to accept the lancet 10', the disposable lancet 15, the special disposable lancet 19, the retractable lancet assembly 40, or other suitable lancets. With reference to FIG. 4, the pimple drain member 12 has the shape of a round bottomed bore 26. A cushion pad 23 is fastened to the bottom surface 29 of the pimple drain member 12. The cushion pad 23 is fabricated from a material which is compressible yet has memory to return to its original thickness; such a material could be an easily compressible rubber, a close cell foam, or any suitable material. A vertical hole 28 passes through the bottom surface 29 of the pimple drain member 12 and cushion pad 23. A cap 17 may also be included for safety reasons.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

We claim:

1. A replaceable comedone extractor for removal of pimples comprising:

a body having a first end, and a second end;

a pimple drain member being disposed at said first end;

a lancet being fabricated from a sharpened metal tip, said lancet being disposed at said second end; and a cushion pad being fastened to a bottom of said pimple drain member.

2. The replaceable comedone extractor for removal of pimples of claim 1, further comprising:

said body having a top surface, a bottom surface, and a substantially middle region which is shaped to be held by a thumb and forefinger, said substantially middle region being rough on said top surface and said bottom surface to improve retention between the thumb and forefinger of a hand.

3. The replaceable comedone extractor for removal of pimples of claim 1, further comprising:

said pimple drain member having a bottom surface, a round bottom bore, and a vertical hole which originates at said round bottom bore, said vertical hole passes through said bottom surface of said pimple drain member and said cushion pad.

4. The replaceable comedone extractor for removal of pimples of claim 1, wherein:

said body being fabricated from a plastic material.

5. The replaceable comedone extractor for removal of pimples of claim 1, further comprising:

a cap being sized to firmly receive said second end of said body.

6. A replaceable comedone extractor for removal of pimples comprising:

a body having a first end and a second end;

a pimple drain member being disposed at said first end;

said body having a horizontal slot formed at said second end, said horizontal slot being sized to firmly receive a disposal lancet;

said body having at least one retaining notch formed at said second end, said retaining notch being sized to receive a longitudinal channel of said disposable lancet, said retaining notch preventing lateral movement of said disposable lancet; and a cushion pad being fastened to a bottom of said pimple drain member.

7. The replaceable comedone extractor for removal of pimples of claim 6, further comprising:

said body having a top surface, a bottom surface, and a substantially middle region which is sized to be held by a thumb and forefinger, said substantially middle region being rough on said top surface and said bottom surface to improve retention between the thumb and forefinger of a hand.

8. The replaceable comedone extractor for removal of pimples of claim 6, further comprising:

said pimple drain member having a bottom surface, a round bottom bore, and a vertical hole which originates at said round bottom bore, said vertical hole passing through said bottom surface of said pimple drain member and said pimple drain member.

9. A replaceable comedone extractor for removal of pimples comprising:

a body having a first end and a second end;

a pimple drain member being disposed at said first end;

a retractable lancet assembly having a first end, a lancet and a retractable cover being forced into a closed position by a spring, said lancet being exposed when said retractable cover is pushed back;

a shaft having a first end, a second end, and a shoulder, said lancet being formed into said second end of said shaft, said lancet protruding from said second end of said shaft;

said retractable cover having a first end, a second end, a first bore originating at said first end, a second bore originating at said second end, and a lip at said first end, said first bore being sized to loosely receive said shoulder of said shaft, said second bore being sized to slidably receive said second end of said shaft, an inner diameter of said lip and an outer diameter of said shoulder being sized to allow said retractable cover to be snapped over said shaft; and said body having a horizontal bore disposed at said second end thereof, said horizontal bore being sized to firmly receive said first end of said retractable lancet assembly.

10. The replaceable comedone extractor for removal of pimples of claim 9, further comprising:

said pimple drain member having a generally round bottom bore, and a vertical hole which originates at said round bottom bore, said vertical hole passing through said bottom surface of said pimple drain member and said cushion pad.

11. The replaceable comedone extractor for removal of pimples of claim 9, further comprising:

said body having a top surface, a bottom surface, and a substantially middle region which is sized to be held by a thumb and forefinger, said substantially middle region being rough on said top surface and said bottom surface to improve retention between the thumb and forefinger of a hand.

12. An angled replaceable comedone extractor for removal of pimples comprising:

an angled body having a first end, and a second end, said second end being bent toward said first end at an obtuse angle;

a pimple drain member being disposed at said first end;

a cushion pad being fastened to a bottom of said pimple drain member; and a lancet being disposed at said second end.

13. The angled replaceable comedone extractor for removal of pimples of claim 12, further comprising:

said angled body having a top surface and a bottom surface; and at least one rib being formed on said top surface to position a thumb.

14. The angled replaceable comedone extractor for removal of pimples of claim 12, further comprising:

said pimple drain member having a bottom surface, a round bottom bore, and a vertical hole which originates at said round bottom bore, said vertical hole passing through said bottom surface of said pimple drain member and said pimple drain member.

15. The angled replaceable comedone extractor for removal of pimples of claim 12, wherein:

said lancet being molded into said second end of said body, said lancet being fabricated from a sharpened rod material.

16. The angled replaceable comedone extractor for removal of pimples of claim 12, wherein:

said lancet being molded into said second end of said body, said lancet being fabricated from a flat sharpened material.

17. The angled replaceable comedone extractor for removal of pimples of claim 12, wherein:

said second end of said body being molded into the shape of a lancet.

18. The angled replaceable comedone extractor for removal of pimples of claim 12, wherein:

said body being fabricated from a plastic material.

19. The angled replaceable comedone extractor for removal of pimples of claim 12, further comprising:

a cap being sized to firmly receive said second end of said body, wherein said cap protects said lancet from damage.

20. An angled replaceable comedone extractor for removal of pimples comprising:

an angled body having a first end, and a second end, said second end being bent toward said first end at an obtuse angle;

a pimple drain member being disposed at said first end;

a cushion pad being fastened to a bottom of said pimple drain member;

said body having a horizontal slot formed at said second end, said horizontal slot being sized to firmly receive a disposal lancet; and said body having at least one retaining notch formed at said second end, said retaining notch being sized to receive a longitudinal channel of said disposable lancet, said retaining notch preventing lateral movement of said disposable lancet.

21. The angled replaceable comedone extractor for removal of pimples of claim 20, further comprising:

said angled body having a top surface and a bottom surface; and at least one rib being formed on said top surface to position a thumb.

22. The angled replaceable comedone extractor for removal of pimples of claim 20, further comprising:

said pimple drain member having a bottom surface, a round bottom bore, and a vertical hole which originates at said round bottom bore, said vertical hole passing through said bottom surface of said pimple drain member and said pimple drain member.

\* \* \* \* \*

UNITED STATES PATENT AND TRADEMARK OFFICE
CERTIFICATE OF CORRECTION

PATENT NO : 5,910,147
DATED : June 8, 1999
INVENTOR(S) : Rosenberg, et al.

It is certified that error appears in the above-identified patent and that said Letters Patent is hereby corrected as shown below:

Title page, item [73]

Assignee: cancel "Ersler; Donald J. (Brookfield, WI)"

insert "[a blank space]"

Signed and Sealed this

Eighth Day of February, 2000

Attest:

Q. TODD DICKINSON

*Attesting Officer*    *Commissioner of Patents and Trademarks*